(12) United States Patent
Tang et al.

(10) Patent No.: US 10,111,428 B2
(45) Date of Patent: Oct. 30, 2018

(54) NEMATOCIDE CONTAINING LACTONIC RING AND PREPARATION METHOD AND APPLICATION THEREOF

(71) Applicant: SHANDONG UNITED PESTICIDE INDUSTRY CO., LTD., Jinan, Shandong (CN)

(72) Inventors: Jianfeng Tang, Jinan (CN); Guangmin Pan, Jinan (CN); Jie Liu, Jinan (CN); Gongwen Zhao, Jinan (CN); Jianting Wu, Jinan (CN); Dongrong Li, Jinan (CN); Fang Niu, Jinan (CN)

(73) Assignee: SHANDONG UNITED PESTICIDE INDUSTRY CO., LTD., Shandong (CN)

( * ) Notice: Subject to any disclaimer, the term of this patent is extended or adjusted under 35 U.S.C. 154(b) by 0 days.

(21) Appl. No.: 15/572,669

(22) PCT Filed: Jun. 20, 2016

(86) PCT No.: PCT/CN2016/086426
§ 371 (c)(1),
(2) Date: Nov. 8, 2017

(87) PCT Pub. No.: WO2017/054523
PCT Pub. Date: Apr. 6, 2017

(65) Prior Publication Data
US 2018/0146667 A1    May 31, 2018

(30) Foreign Application Priority Data
Sep. 30, 2015   (CN) .......................... 2015 1 0645033

(51) Int. Cl.
*A01N 43/08* (2006.01)
*C07D 307/33* (2006.01)
*A01N 25/02* (2006.01)
(52) U.S. Cl.
CPC ............. *A01N 43/08* (2013.01); *A01N 25/02* (2013.01); *C07D 307/33* (2013.01)

(58) Field of Classification Search
CPC ....... A01N 43/08; A01N 25/02; C07D 307/33
See application file for complete search history.

(56) References Cited

U.S. PATENT DOCUMENTS

2005/0113366 A1   5/2005   Bourguignon et al.

FOREIGN PATENT DOCUMENTS

| CN | 1545507 A | 11/2004 | |
|---|---|---|---|
| CN | 103408517 A | 11/2013 | |
| EP | 0692191 A1 * | 1/1996 | ............. A01N 31/14 |

OTHER PUBLICATIONS

Sep. 30, 2016 Written Opinion issued in International Patent Application No. PCT/CN2016/086426.
Zhiqiang Li et al; "Copper-catalyzed domino reactions: conjugate alkylative aldol addition/lactonization of a,b-unsaturated diesters"; Tetrahedron Letters; vol. 56; 2015; pp. 5541-5544.
Sep. 30, 2016 International Search Report issued in International Patent Application No. PCT/CN2016/086426.

* cited by examiner

*Primary Examiner* — Abigail Vanhorn
*Assistant Examiner* — Nathan W Schlientz
(74) *Attorney, Agent, or Firm* — Oliff PLC

(57) ABSTRACT

A nematocide containing lactonic ring and a preparation method and application thereof. The nematocide containing lactonic ring includes hydrogen, cyan, fluorine, chlorine, bromine, alkyl containing 1 to 4 carbon atoms, alkoxy containing 1 to 4 carbon atoms, alkoxyphenyl, alkoxy containing 1 to 4 carbon atoms and one or more chlorine atoms in place of hydrogen atoms on the carbon atoms, alkoxy containing 1 to 4 carbon atoms and one or more fluorine atoms in place of hydrogen atoms on the carbon atoms, nitryl, and amido; $R_6$ is selected from hydrogen, fluorine and chlorine. A result is good control effects on the eggs and second-stage juveniles of root-knot nematodes, and especially inhibition of the hatch of root-knot nematode eggs on cucumbers, tomatoes, tobaccos and soybeans, etc. The nematocide has high insecticidal efficacy and can prevent the production of antibodies in pests even after a long time of use.

8 Claims, No Drawings

NEMATOCIDE CONTAINING LACTONIC RING AND PREPARATION METHOD AND APPLICATION THEREOF

TECHNICAL FIELD

The present invention relates to the technical field of agricultural chemistry and medicine, and specifically to a nematocide containing lactonic ring and a preparation method and application thereof.

BACKGROUND ART

Most nematodes live in soil, while some parasitize in plants. They are transmitted by soil or seeds. They can destroy the root system of plants, invade into their above-ground organs, and indirectly spread diseases caused by other microorganisms, thus affecting the growth of crops, and leading to great economic losses in agriculture. The existing nematocides in the world permeate through the epicuticle of nematodes.

Among them only a dozen of nematocides are effective. However, their use is influenced as they have high toxicity to humans and animals and some of them are harmful to crops. Therefore, a novel, efficient and environment-friendly nematocide is urgent to be developed.

SUMMARY

Aiming to solve the problems of the existing technology, the present invention provides a nematocide containing lactonic ring and a preparation method and application thereof. The nematocide containing lactonic ring in the present invention has good insecticidal activity and low toxicity to humans and animals.

To realize the above purpose, the present invention adopts the following technical scheme.

A nematocide containing lactonic ring has a general structural formula I as follows:

General structural formula I

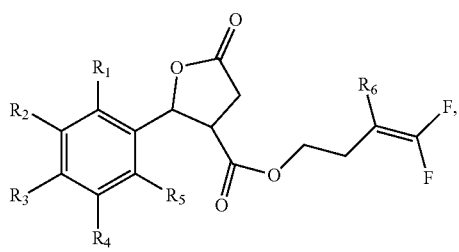

wherein $R_1$, $R_2$, $R_3$, $R_4$ and $R_5$ are selected from hydrogen, cyan, fluorine, chlorine, bromine, alkyl containing 1 to 4 carbon atoms, alkoxy containing 1 to 4 carbon atoms, alkoxyphenyl, alkoxy containing 1 to 4 carbon atoms and one or more chlorine atoms in place of hydrogen atoms on the carbon atoms, alkoxy containing 1 to 4 carbon atoms and one or more fluorine atoms in place of hydrogen atoms on the carbon atoms, nitryl, or amido;

$R_6$ is selected from hydrogen, fluorine and chlorine.

Preferentially, a nematocide containing lactonic ring, wherein $R_6$ is fluorine atom.

Preferentially, a nematocide containing lactonic ring, wherein when $R_1$=$CF_3$, $R_2$=$R_3$=$R_4$=$R_5$=H.

Preferentially, a nematocide containing lactonic ring, wherein when $R_1$=$OCF_3$, $R_2$=$R_3$=$R_4$=$R_5$=H.

Preferentially, a nematocide containing lactonic ring, wherein when R1=R2=R5=H, $R_3$=F, $R_4$=—O—$C_6H_5$.

Preferentially, a nematocide containing lactonic ring, wherein when $R_2$=$R_4$=$CF_3$, $R_1$=$R_3$=$R_5$=H.

The present invention further provides a method for preparing the nematocide containing lactonic ring, comprising the following steps of: adding

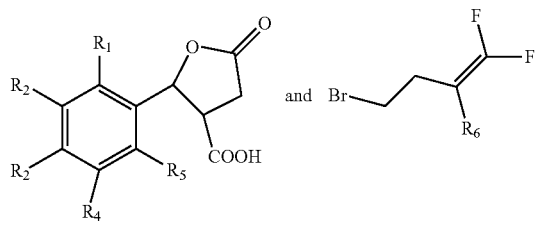

into a solvent, and adding an acid-binding agent; maintaining a stirring reaction for 22 to 26 hours under 20 to 30° C.; distilling under the vacuum degree of 0.08 to 0.10 kPa to remove the solvent; adding methylene dichloride and water, and evenly stirring; carrying out static stratification to remove water; and distilling under the vacuum degree of 0.08 to 0.10 kPa to remove the methylene dichloride, thus obtaining the nematocide containing lactonic ring, as shown in general formula I, wherein

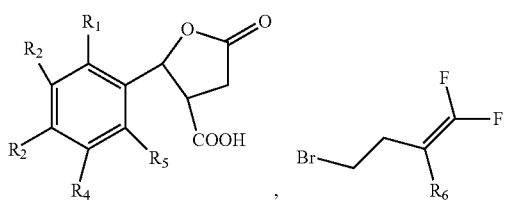

and the acid-binding agent have a molar ratio of 1:0.8 to 1.2:3 to 5;

$R_1$, $R_2$, $R_3$, $R_4$ and $R_5$ are selected from hydrogen, cyan, fluorine, chlorine, bromine, alkyl containing 1 to 4 carbon atoms, alkoxy containing 1 to 4 carbon atoms, alkoxyphenyl, alkoxy containing 1 to 4 carbon atoms and one or more chlorine atoms in place of hydrogen atoms on the carbon atoms, alkoxy containing 1 to 4 carbon atoms and one or more fluorine atoms in place of hydrogen atoms on the carbon atoms, nitryl, and amido; $R_6$ is selected from hydrogen, fluorine and chlorine;

the solvent is methyl alcohol, ethyl alcohol, acetone, N,N-dimethylformamide or N,N-dimethylformamide; the acid-binding agent is potassium carbonate, sodium carbonate, pyridine or triethylamine.

The present invention further provides an application of the nematocide containing lactonic ring, wherein the nematocide is used to control nematode diseases in agriculture.

The present invention has the following advantages:

Containing lactonic ring and polyfluorobutylene, the nematocide in the present invention has good control effects on the eggs and second-stage juveniles of root-knot nematodes, and especially can well inhibit the hatch of root-knot nematode eggs on cucumbers, tomatoes, tobaccos and soybeans, etc. Besides, the nematocide containing lactonic ring has low toxicity, low residue on crops and small hazard to humans and animals, thus well solving the problems that the existing nematocides have high toxicity and high residue on crops, and improving agricultural production safety. The nematocide has high insecticidal efficacy and can prevent the production of antibodies in pests even after a long time of use. The present invention further provides a preparation method for the nematocide containing lactonic ring. The preparation method has short steps and simple process, and is suitable for large-scale industrial production.

DESCRIPTION OF EMBODIMENTS

A nematocide containing lactonic ring has a general structural formula I as follows:

General structural formula I

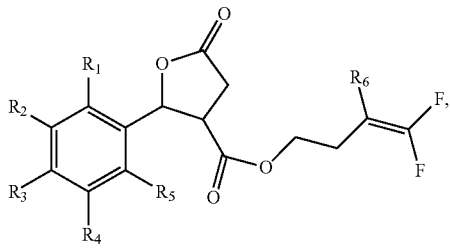

wherein $R_1$, $R_2$, $R_3$, $R_4$ and $R_5$ are selected from hydrogen, cyan, fluorine, chlorine, bromine, alkyl containing 1 to 4 carbon atoms, alkoxy containing 1 to 4 carbon atoms, alkoxyphenyl, alkoxy containing 1 to 4 carbon atoms and one or more chlorine atoms in place of hydrogen atoms on the carbon atoms, alkoxy containing 1 to 4 carbon atoms and one or more fluorine atoms in place of hydrogen atoms on the carbon atoms, nitryl, or amido;

$R_6$ is selected from hydrogen, fluorine and chlorine.

Preferentially, a nematocide containing lactonic ring, wherein $R_6$ is fluorine atom.

Preferentially, a nematocide containing lactonic ring, wherein when $R_1=CF_3$, $R_2=R_3=R_4=R_5=H$.

Preferentially, a nematocide containing lactonic ring, wherein when $R_1=OCF_3$, $R_2=R_3=R_4=R_5=H$.

Preferentially, a nematocide containing lactonic ring, wherein when R1=R2=R5=H, $R_3=F$, $R_4=$—O—$C_6H_5$.

Preferentially, a nematocide containing lactonic ring, wherein when $R_2=R_4=CF_3$, $R_1=R_3=R_5=H$.

The present invention further provides a method for preparing the nematocide containing lactonic ring, comprising the following steps of: adding

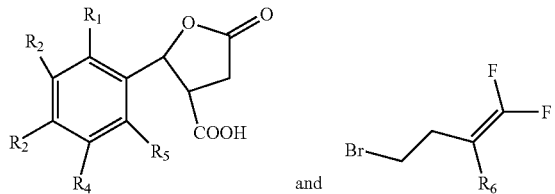

into a solvent, and adding an acid-binding agent; maintaining a stirring reaction for 22 to 26 hours under 20 to 30° C.; distilling under the vacuum degree of 0.08 to 0.10 kPa to remove the solvent; adding methylene dichloride and water, and evenly stirring; carrying out static stratification to remove water; and distilling under the vacuum degree of 0.08 to 0.10 kPa to remove the methylene dichloride, thus obtaining the nematocide containing lactonic ring, as shown in general formula I, wherein

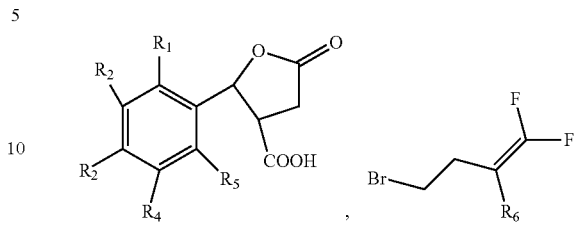

and the acid-binding agent have a molar ratio of 1:0.8 to 1.2:3 to 5;

$R_1$, $R_2$, $R_3$, $R_4$ and $R_5$ are selected from hydrogen, cyan, fluorine, chlorine, bromine, alkyl containing 1 to 4 carbon atoms, alkoxy containing 1 to 4 carbon atoms, alkoxyphenyl, alkoxy containing 1 to 4 carbon atoms and one or more chlorine atoms in place of hydrogen atoms on the carbon atoms, alkoxy containing 1 to 4 carbon atoms and one or more fluorine atoms in place of hydrogen atoms on the carbon atoms, nitryl, and amido; $R_6$ is selected from hydrogen, fluorine and chlorine;

the reaction formula is:

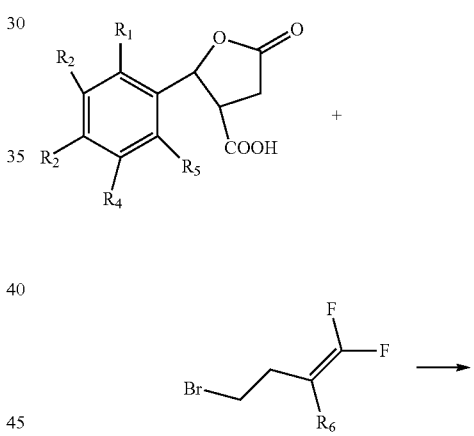

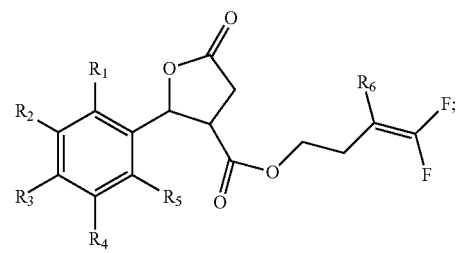

the solvent is methyl alcohol, ethyl alcohol, acetone, N,N-dimethylformamide or N,N-dimethylformamide; the acid-binding agent is potassium carbonate, sodium carbonate, pyridine or triethylamine.

The present invention further provides an application of the nematocide containing lactonic ring, wherein the nematocide is used to control nematode diseases in agriculture.

In the present invention, the raw material

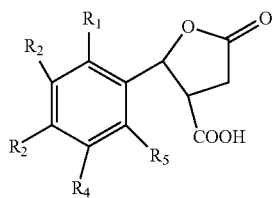

of the preparation method can either be purchased from the market, or be prepared according to the following steps of: sequentially adding

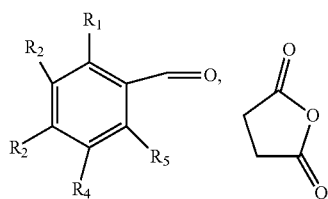

and anhydrous zinc chloride into methylene dichloride; dropping triethylamine under 0 to 5° C. to produce reaction liquid; stirring the reaction liquid under 20 to 30° C. for 10 to 20 hours; adding hydrochloric acid into the reaction liquid till the pH reaches 2; adding ethyl acetate and extracting; collecting the organic phase; and adding methylbenzene for recrystallization, and obtaining

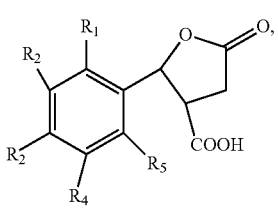

wherein

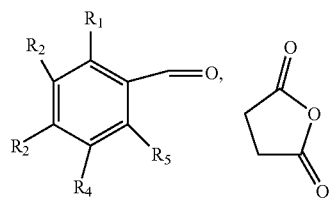

and anhydrous zinc chloride have a molar ratio of 1:0.8 to 1.2:1 to 3:3 to 5; the reaction formula is:

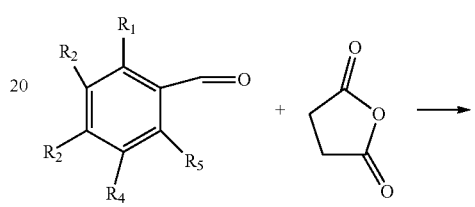

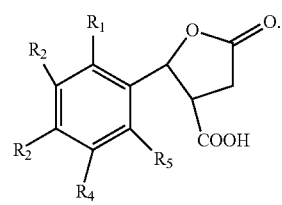

TABLE 1

Structural measurement analysis of compounds of nematocide containing lactonic ring Formula I

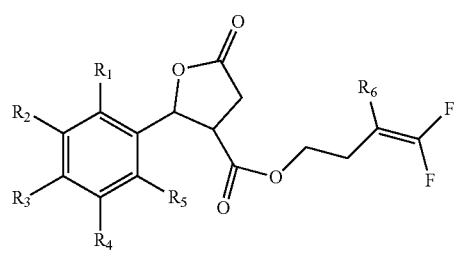

| S/N | R1 | R2 | R3 | R4 | R5 | R6 m/z |
|---|---|---|---|---|---|---|
| 1 | H | H | H | H | H | H m/z: 296.09 (100.0%), 297.09 (16.5%), 298.09 (2.1%) |
| 2 | $CH_3$ | H | H | H | H | H m/z: 310.10 (100.0%), 311.11 (17.6%), 312.11 (2.3%) |
| 3 | H | H | $CH_3$ | H | H | H m/z: 310.10 (100.0%), 311.11 (17.6%), 312.11 (2.3%) |

TABLE 1-continued

Structural measurement analysis of compounds of nematocide containing lactonic ring Formula I

| S/N | R1 | R2 | R3 | R4 | R5 | R6 | m/z |
|-----|----|----|----|----|----|----|-----|
| 4 | H | H | C$_2$H$_5$ | H | H | H | m/z: 324.12 (100.0%), 325.12 (18.7%), 326.12 (2.4%) |
| 5 | H | H | C$_3$H$_7$ | H | H | F | m/z: 356.12 (100.0%), 357.13 (19.8%), 358.13 (2.7%) |
| 6 | H | H | C$_4$H$_9$ | H | H | F | m/z: 370.14 (100.0%), 371.14 (20.7%), 372.15 (2.1%) |
| 7 | Cl | H | H | H | H | F | m/z: 348.04 (100.0%), 350.03 (32.0%), 349.04 (16.5%), 351.04 (5.3%), 350.04 (2.1%) |
| 8 | Cl | Cl | H | H | H | F | m/z: 382.00 (100.0%), 384.00 (64.7%), 383.00 (16.5%), 385.00 (10.5%), 385.99 (10.2%), 387.00 (1.8%), 386.00 (1.3%), 384.01 (1.3%) |
| 9 | Cl | H | Cl | H | H | F | m/z: 382.00 (100.0%), 384.00 (64.7%), 383.00 (16.5%), 385.00 (10.5%), 385.99 (10.2%), 387.00 (1.8%), 386.00 (1.3%), 384.01 (1.3%) |
| 10 | Cl | H | H | Cl | H | F | m/z: 382.00 (100.0%), 384.00 (64.7%), 383.00 (16.5%), 385.00 (10.5%), 385.99 (10.2%), 387.00 (1.8%), 386.00 (1.3%), 384.01 (1.3%) |
| 11 | Cl | H | H | H | Cl | F | m/z: 382.00 (100.0%), 384.00 (64.7%), 383.00 (16.5%), 385.00 (10.5%), 385.99 (10.2%), 387.00 (1.8%), 386.00 (1.3%), 384.01 (1.3%) |
| 12 | Cl | Cl | H | Cl | H | F | m/z: 415.96 (100.0%), 417.96 (96.7%), 419.95 (30.6%), 416.96 (16.4%), 418.96 (15.8%), 420.96 (5.2%), 421.95 (3.3%), 419.96 (2.0%), 417.97 (1.3%) |
| 13 | H | Cl | H | Cl | H | F | m/z: 382.00 (100.0%), 384.00 (64.7%), 383.00 (16.5%), 385.00 (10.5%), 385.99 (10.2%), 387.00 (1.8%), 386.00 (1.3%), 384.01 (1.3%) |
| 14 | H | Cl | H | H | H | F | m/z: 348.04 (100.0%), 350.03 (32.0%), 349.04 (16.5%), 351.04 (5.3%), 350.04 (2.1%) |
| 15 | H | H | Cl | H | H | F | m/z: 348.04 (100.0%), 350.03 (32.0%), 349.04 (16.5%), 351.04 (5.3%), 350.04 (2.1%) |
| 16 | Cl | H | H | H | F | F | m/z: 366.03 (100.0%), 368.03 (34.0%), 367.03 (16.5%), 369.03 (5.3%) |
| 17 | H | H | Br | H | H | F | m/z: 471.90 (100.0%), 469.90 (50.9%), 473.89 (48.1%), 472.90 (16.3%), 470.90 (8.4%), 474.90 (8.1%), 473.90 (2.1%), 475.90 (1.0%) |
| 18 | H | Br | H | Br | H | F | m/z: 471.90 (100.0%), 469.90 (50.9%), 473.89 (48.1%), 472.90 (16.3%), 470.90 (8.4%), 474.90 (8.1%), 473.90 (2.1%), 475.90 (1.0%) |
| 19 | F | H | H | H | H | F | m/z: 332.07 (100.0%), 333.07 (16.5%), 334.07 (2.1%) |

TABLE 1-continued

Structural measurement analysis of compounds of nematocide containing lactonic ring Formula I

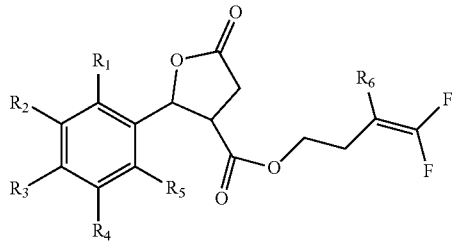

| S/N | R1 | R2 | R3 | R4 | R5 | R6 | m/z |
|---|---|---|---|---|---|---|---|
| 20 | H | H | F | H | H | F | m/z: 332.07 (100.0%), 333.07 (16.5%), 334.07 (2.1%) |
| 21 | F | H | Cl | H | H | F | m/z: 366.03 (100.0%), 368.03 (34.0%), 367.03 (16.5%), 369.03 (5.3%) |
| 22 | H | F | H | Br | H | F | m/z: 409.98 (100.0%), 411.98 (99.3%), 410.98 (16.5%), 412.98 (16.1%), 413.98 (2.0%) |
| 23 | H | Cl | F | H | H | F | m/z: 366.03 (100.0%), 368.03 (34.0%), 367.03 (16.5%), 369.03 (5.3%) |
| 24 | H | Cl | H | F | H | F | m/z: 366.03 (100.0%), 368.03 (34.0%), 367.03 (16.5%), 369.03 (5.3%) |
| 25 | F | H | Br | H | H | F | m/z: 409.98 (100.0%), 411.98 (99.3%), 410.98 (16.5%), 412.98 (16.1%), 413.98 (2.0%) |
| 26 | H | H | F | 3-CF$_3$-phenoxy | H | F | m/z: 442.08 (100.0%), 443.09 (23.1%), 444.09 (3.6%) |
| 27 | H | F | H | H | H | F | m/z: 332.07 (100.0%), 333.07 (16.5%), 334.07 (2.1%) |
| 28 | F | H | H | F | H | F | m/z: 350.06 (100.0%), 351.06 (16.5%), 352.06 (2.1%) |
| 29 | F | F | F | F | F | F | m/z: 404.03 (100.0%), 405.03 (16.4%), 406.04 (1.3%) |
| 30 | H | F | F | F | H | F | m/z: 368.05 (100.0%), 369.05 (16.5%), 370.06 (1.3%) |
| 31 | F | H | H | H | CF$_3$ | F | m/z: 400.05 (100.0%), 401.06 (17.6%), 402.06 (2.3%) |
| 32 | F | H | CF$_3$ | H | H | F | m/z: 400.05 (100.0%), 401.06 (17.6%), 402.06 (2.3%) |
| 33 | H | F | OCH$_3$ | F | H | F | m/z: 380.07 (100.0%), 381.07 (17.6%), 382.08 (1.5%), 382.07 (1.0%) |
| 34 | OCH$_3$ | H | H | H | H | H | m/z: 326.10 (100.0%), 327.10 (17.7%), 328.10 (2.5%) |
| 35 | OCH$_3$ | H | H | H | H | F | m/z: 344.09 (100.0%), 345.09 (17.7%), 346.09 (2.5%) |
| 36 | H | OCH$_3$ | H | H | H | H | m/z: 326.10 (100.0%), 327.10 (17.7%), 328.10 (2.5%) |
| 37 | H | OCH$_3$ | H | H | H | F | m/z: 344.09 (100.0%), 345.09 (17.7%), 346.09 (2.5%) |
| 38 | H | H | OCH$_3$ | H | H | H | m/z: 326.10 (100.0%), 327.10 (17.7%), 328.10 (2.5%) |
| 39 | H | H | OCH$_3$ | H | H | F | m/z: 344.09 (100.0%), 345.09 (17.7%), 346.09 (2.5%) |
| 40 | OCF$_3$ | H | H | H | H | H | m/z: 380.07 (100.0%), 381.07 (17.6%), 382.08 (1.5%), 382.07 (1.0%) |
| 41 | OCF$_3$ | H | H | H | H | F | m/z: 398.06 (100.0%), 399.06 (17.5%), 400.07 (1.5%), 400.06 (1.0%) |
| 42 | CF$_3$ | H | OCH$_3$ | H | H | F | m/z: 412.07 (100.0%), 413.08 (18.7%), 414.08 (2.7%) |
| 43 | OCH$_2$CH$_3$ | H | H | H | H | F | m/z: 358.10 (100.0%), 359.11 (18.8%), 360.11 (2.7%) |

TABLE 1-continued

Structural measurement analysis of compounds of nematocide containing lactonic ring Formula I

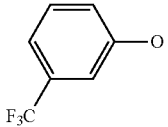

| S/N | R1 | R2 | R3 | R4 | R5 | R6 | m/z |
|---|---|---|---|---|---|---|---|
| 44 | H | H | OCH$_2$CH$_3$ | H | H | F | m/z: 358.10 (100.0%), 359.11 (18.8%), 360.11 (2.7%) |
| 45 | CF$_3$ | H | H | H | H | H | m/z: 364.07 (100.0%), 365.08 (17.6%), 366.08 (2.3%) |
| 46 | CF$_3$ | H | H | H | H | F | m/z: 382.06 (100.0%), 383.07 (17.6%), 384.07 (2.3%) |
| 47 | H | CF$_3$ | H | CF$_3$ | H | H | m/z: 432.06 (100.0%), 433.06 (18.4%), 434.07 (2.5%) |
| 48 | H | CF$_3$ | H | CF$_3$ | H | F | m/z: 450.05 (100.0%), 451.05 (18.4%), 452.06 (2.5%) |
| 49 | H | H | CN | H | H | F | m/z: 339.07 (100.0%), 340.08 (17.6%), 341.08 (2.3%) |
| 50 | H | 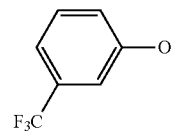 | H | H | H | F | m/z: 406.10 (100.0%), 407.11 (23.1%), 408.11 (3.6%) |
| 51 | H | H | 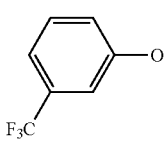 | H | H | F | m/z: 406.10 (100.0%), 407.11 (23.1%), 408.11 (3.6%) |
| 52 | H | 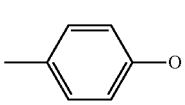 | H | H | H | F | m/z: 474.09 (100.0%), 475.09 (24.0%), 476.10 (2.8%), 476.09 (1.0%) |
| 53 | 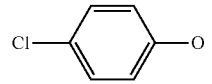 | H | H | H | H | F | m/z: 420.12 (100.0%), 421.12 (24.2%), 422.13 (2.8%), 422.12 (1.0%) |
| 54 | H | H | 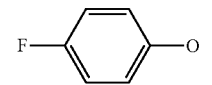 | H | H | F | m/z: 440.06 (100.0%), 442.06 (32.0%), 441.07 (23.1%), 443.06 (7.3%), 442.07 (3.6%), 444.07 (1.2%) |
| 55 | H | H | 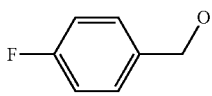 | H | H | F | m/z: 424.09 (100.0%), 425.10 (23.1%), 426.10 (3.6%) |
| 56 | H | H |  | H | H | F | m/z: 438.11 (100.0%), 439.11 (24.0%), 440.12 (2.8%), 440.11 (1.0%) |
| 57 | H | NO$_2$ | H | H | H | F | m/z: 359.06 (100.0%), 360.07 (16.6%), 361.07 (2.5%) |
| 58 | H | H | NO$_2$ | H | H | F | m/z: 359.06 (100.0%), 360.07 (16.6%), 361.07 (2.5%) |
| 59 | NH$_2$ | H | H | H | H | F | m/z: 329.09 (100.0%), 330.09 (16.5%), 331.09 (2.1%) |

TABLE 1-continued

Structural measurement analysis of compounds of nematocide containing lactonic ring

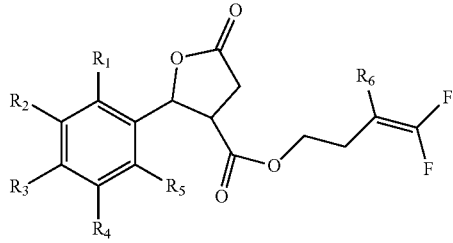

Formula I

| S/N | R1 | R2 | R3 | R4 | R5 | R6 | m/z |
|---|---|---|---|---|---|---|---|
| 60 | H | H | $NH_2$ | H | H | F | m/z: 329.09 (100.0%), 330.09 (16.5%), 331.09 (2.1%) |

In the present invention, the nematocide containing lactonic ring can be prepared by the preparation method. The following are embodiments of the compounds in Table 1:

Embodiment 1

Compound 2 in Table 1 is prepared according to the following steps:

① Adding 1 mol o-methylbenzaldehyde, 0.8 mol succinic anhydride and 1 mol anhydrous zinc chloride into 300 ml methylene dichloride; dropping 3 mol triethylamine under 0° C. to produce reaction liquid; stirring the reaction liquid under 20° C. for 10 h; then adding hydrochloric acid into the reaction liquid till the pH reaches 2; adding 200 ml ethyl acetate and extracting; collecting the organic phase; adding 200 ml methylbenzene into the organic phase for recrystallization, and obtaining 5-oxo-2-(2-methylphenyl)tetrahydrofuran-3-carboxylic acid;

② Adding 0.5 mol 5-oxo-2-(2-methylphenyl)tetrahydrofuran-3-carboxylic acid produced in step ① and 0.4 mol 4-bromine-1,1-difluoro-1-butylene into 500 ml methyl alcohol; adding 1.5 mol potassium carbonate; stirring under 20° C. for 22 hours; distilling under the vacuum degree of 0.08 kPa to remove the methyl alcohol; adding the residues into 100 ml methylene dichloride and 50 ml water; evenly stirring; carrying out static stratification; collecting the methylene dichloride phase; and distilling the collected phase under the vacuum degree of 0.08 kPa, and obtaining the product, i.e. compound 2 in Table 1.

Element analysis results: C, 61.93; H, 5.20; F, 12.25; O, 20.62.

Nuclear magnetic resonance analysis results: δ2.24, 2H; δ2.34, 3H; δ2.52-2.77, 2H; δ3.31, 1H; δ4.12, 2H; δ4.28, 1H; δ6.21, 1H; δ7.19-7.26, 3H; δ7.39, 1H.

Embodiment 2

Compound 26 in Table 1 is prepared according to the following steps:

① Adding 1 mol 4-fluoro-5-phenoxybenzaldehyde, 1.2 mol succinic anhydride and 3 mol anhydrous zinc chloride into 400 ml methylene dichloride; dropping 5 mol triethylamine under 5° C. to produce reaction liquid; stirring the reaction liquid under 30° C. for 20 h; then adding hydrochloric acid into the reaction liquid till the pH reaches 2; adding 250 ml ethyl acetate and extracting; collecting the organic phase; adding 250 ml methylbenzene into the organic phase for recrystallization, and obtaining 5-oxo-2-(2-(4-fluoro-5-phenoxyl)phenyl)tetrahydrofuran-3-carboxylic acid;

② Adding 0.5 mol 5-oxo-2-(2-(4-fluoro-5-phenoxyl) phenyl) tetrahydrofuran-3-carboxylic acid produced in step ① and 0.6 mol 4-bromine-1,1-difluoro-1-butylene into 400 ml ethyl alcohol; adding 2.5 mol sodium carbonate; stirring under 30° C. for 26 hours; distilling under the vacuum degree of 0.10 kPa to remove the ethyl alcohol; adding the residues into 120 ml methylene dichloride and 80 ml water; evenly stirring; carrying out static stratification; collecting the methylene dichloride phase; and distilling the collected phase under the vacuum degree of 0.12 kPa, and obtaining the product, i.e. compound 26 in Table 1.

Element analysis results: C, 59.44; H, 3.80; F, 17.91; O, 18.85.

Nuclear magnetic resonance analysis results: δ2.24, 2H; δ2.52-2.77, 2H; δ3.31, 1H; δ4.12, 2H; δ6.21, 1H; δ7.06-7.14, 5H; δ7.27, 1H; δ7.41, 2H.

Embodiment 3

Compound 41 in Table 1 is prepared according to the following steps:

① Adding 1 mol o-trifluoromethylbenzaldehyde, 1 mol succinic anhydride and 2 mol anhydrous zinc chloride into 300 ml methylene dichloride; dropping 4 mol triethylamine under 5° C. to produce reaction liquid; stirring the reaction liquid under 25° C. for 15 h; then adding hydrochloric acid into the reaction liquid till the pH reaches 2; adding 220 ml ethyl acetate and extracting; collecting the organic phase; adding 220 ml methylbenzene into the organic phase for recrystallization, and obtaining 5-oxo-2-(2-trifluoromethoxy)phenyl)tetrahydrofuran-3-carboxylic acid;

② Adding 0.5 mol 5-oxo-2-(2-trifluoromethoxy) phenyl) tetrahydrofuran-3-carboxylic acid produced in step ① and 0.5 mol 4-bromine-1,1,2-trifluoro-1-butylene into 380 ml acetone; adding 2.0 mol pyridine; stirring under 25° C. for 24 hours; distilling under the vacuum degree of 0.10 kPa to remove the acetone; adding the residues into 120 ml methylene dichloride and 100 ml water; evenly stirring; carrying out static stratification; collecting the methylene dichloride phase; and distilling the collected phase under the vacuum degree of 0.10 kPa, and obtaining the product, i.e. compound 41 in Table 1.

Element analysis results: C, 48.25; H, 3.04; F, 28.62; O, 20.09.

Nuclear magnetic resonance analysis results: δ2.24, 2H; δ2.52-2.77, 2H; δ3.31, 1H; δ4.12, 2H; δ6.21, 1H; δ6.92-6.96, 3H; δ7.25, 1H.

Embodiment 4

Compound 46 in Table 1 is prepared according to the following steps:

① Adding 1 mol o-trifluoromethylbenzaldehyde, 1.1 mol succinic anhydride and 2.5 mol anhydrous zinc chloride into 300 ml methylene dichloride; dropping 3.5 mol triethylamine under 3° C. to produce reaction liquid; stirring the reaction liquid under 22° C. for 12 h; then adding hydrochloric acid into the reaction liquid till the pH reaches 2; adding 250 ml ethyl acetate and extracting; collecting the organic phase; adding 250 ml methylbenzene into the organic phase for recrystallization, and obtaining 5-oxo-2-(2-trifluoromethyl)phenyl)tetrahydrofuran-3-carboxylic acid;

① Adding 0.5 mol 5-oxo-2-(2-trifluoromethyl) phenyl) tetrahydrofuran-3-carboxylic acid produced in step ① and 0.5 mol 4-bromine-1,1,2-trifluoro-1-butylene into 380 ml acetone; adding 2.0 mol triethylamine; stirring under 25° C. for 22 hours; distilling under the vacuum degree of 0.10 kPa to remove the acetone; adding the residues into 120 ml methylene dichloride and 100 ml water; evenly stirring; carrying out static stratification; collecting the methylene dichloride phase; and distilling the collected phase under the vacuum degree of 0.10 kPa, and obtaining the product, i.e. compound 46 in Table 1.

Element analysis results: C, 50.28; H, 3.16; F, 29.82; O, 16.73.

Nuclear magnetic resonance analysis results: δ2.24, 2H; δ2.52-2.77, 2H; δ3.31, 1H; δ4.12, 2H; δ6.21, 1H; δ7.29-7.38, 3H; δ7.55, 1H.

Embodiment 5

Compound 48 in Table 1 is prepared according to the following steps:

① Adding 1 mol 3.5-trifluoromethylbenzaldehyde, 0.9 mol succinic anhydride and 2.5 mol anhydrous zinc chloride into 300 ml methylene dichloride; dropping 3.5 mol triethylamine under 4° C. to produce reaction liquid; stirring the reaction liquid under 22° C. for 16 h; then adding hydrochloric acid into the reaction liquid till the pH reaches 2; adding 250 ml ethyl acetate and extracting; collecting the organic phase; adding 250 ml methylbenzene into the organic phase for recrystallization, and obtaining 5-oxo-2-(3,5-bistrifluoromethyl)phenyl)tetrahydrofuran-3-carboxylic acid;

② Adding 0.5 mol 5-oxo-2-(3,5-bistrifluoromethyl) phenyl) tetrahydrofuran-3-carboxylic acid produced in step ① and 0.5 mol 4-bromine-1,1,2-trifluoro-1-butylene into 380 ml acetone; adding 2.0 mol triethylamine; stirring under 25° C. for 22 hours; distilling under the vacuum degree of 0.10 kPa to remove the acetone; adding the residues into 120 ml methylene dichloride and 100 ml water; evenly stirring; carrying out static stratification; collecting the methylene dichloride phase; and distilling the collected phase under the vacuum degree of 0.10 kPa, and obtaining the product, i.e. compound 48 in Table 1.

Element analysis results: C, 45.35; H, 2.46; F, 37.98; O, 14.21.

Nuclear magnetic resonance analysis results: δ2.24, 2H; δ2.52-2.77, 2H; δ3.31, 1H; δ4.12, 2H; δ6.21, 1H; δ7.62, 2H; δ7.94, 1H.

Nematocidal Test

A plant pathogenic nematode inhibition test is conducted by dipping with the compounds in Table 1; and by referring to NY/T 1154.5-2006 (*Part 5: Dipping Test for Insecticide Ovicidal Activity*), the nematode egg hatch inhibition activity of the compounds is tested, as shown in Table 2:

TABLE 2

Plant pathogenic nematode inhibition test results of compounds of nematocide containing lactonic ring

| Reagent | Test Object | Regression Equation | $LC_{50}$ (μg/ml) | Correlation Coefficient ($R^2$) | 95% Confidence Interval |
|---|---|---|---|---|---|
| Compound 1 | Nematode eggs | y = −1.723 + 1.346x | 11.81 | 0.994 | 8.341~11.441 |
|  | Nematode $J_2$ | y = −1.410 + 1.521x | 12.24 | 0.981 | 7.221~13.575 |
| Compound 2 | Nematode eggs | y = −1.782 + 1.796x | 9.81 | 0.998 | 8.374~11.488 |
|  | Nematode $J_2$ | y = −1.696 + 1.687x | 10.14 | 0.971 | 6.221~18.575 |
| Compound 3 | Nematode eggs | y = −1.524 + 1.452x | 10.01 | 0.978 | 9.374~11.898 |
|  | Nematode $J_2$ | y = −1.568 + 1.547x | 10.23 | 0.981 | 6.221~14.215 |
| Compound 4 | Nematode eggs | y = −1.524 + 1.210x | 10.25 | 0.968 | 7.374~10.488 |
|  | Nematode $J_2$ | y = −1.751 + 1.014x | 10.24 | 0.979 | 6.741~18.514 |
| Compound 5 | Nematode eggs | y = −2.446 + 2.705x | 8.02 | 0.87 | 5.728~12.709 |
|  | Nematode $J_2$ | y = −3.150 + 3.181x | 9.777 | 0.973 | 8.938~10.968 |
| Compound 6 | Nematode eggs | y = −1.247 + 1.325x | 11.81 | 0.994 | 8.317~11.414 |
|  | Nematode $J_2$ | y = −1.354 + 1.274x | 13.45 | 0.985 | 8.221~14.135 |
| Compound 7 | Nematode eggs | y = −1.653 + 1.471x | 12.81 | 0.987 | 9.124~11.488 |
|  | Nematode $J_2$ | y = −1.254 + 1.571x | 13.25 | 0.986 | 11.221~18.512 |
| Compound 8 | Nematode eggs | y = −1.417 + 1.086x | 12.81 | 0.986 | 8.374~12.414 |
|  | Nematode $J_2$ | y = −1.147 + 1.541x | 13.14 | 0.989 | 11.221~15.125 |
| Compound 9 | Nematode eggs | y = −1.368 + 1.254x | 10.36 | 0.986 | 8.374~11.424 |
|  | Nematode $J_2$ | y = −1.254 + 1.147x | 13.14 | 0.989 | 6.254~18.145 |
| Compound 10 | Nematode eggs | y = −1.187 + 1.149x | 10.80 | 0.987 | 8.551~13.751 |
|  | Nematode $J_2$ | y = −1.325 + 1.179x | 13.30 | 0.988 | 10.620~17.149 |
| Compound 11 | Nematode eggs | y = −1.859 + 1.534x | 13.30 | 0.993 | 13.597~19.559 |
|  | Nematode $J_2$ | y = −2.075 + 1.624x | 14.95 | 0.996 | 15.971~22.642 |
| Compound 12 | Nematode eggs | y = −1.859 + 1.534x | 12.30 | 0.997 | 12.597~19.009 |
|  | Nematode $J_2$ | y = −2.075 + 1.624x | 13.35 | 0.998 | 13.971~17.612 |
| Compound 13 | Nematode eggs | y = −1.859 + 1.534x | 15.46 | 0.986 | 13.247~15.514 |
|  | Nematode $J_2$ | y = −2.075 + 1.624x | 16.25 | 0.978 | 15.141~20.642 |

TABLE 2-continued

Plant pathogenic nematode inhibition test results of compounds of nematocide containing lactonic ring

| Reagent | Test Object | Regression Equation | LC$_{50}$ (μg/ml) | Correlation Coefficient (R$^2$) | 95% Confidence Interval |
|---|---|---|---|---|---|
| Compound 14 | Nematode eggs | y = −1.859 + 1.534x | 12.10 | 0.983 | 13.047~16.552 |
| | Nematode J$_2$ | y = −2.075 + 1.624x | 13.01 | 0.991 | 14.971~20.612 |
| Compound 15 | Nematode eggs | y = −1.778 + 1.557x | 11.88 | 0.946 | 9.054~24.244 |
| | Nematode J$_2$ | y = −1.530 + 1.203x | 12.69 | 0.984 | 14.796~25.115 |
| Compound 16 | Nematode eggs | y = −1.236 + 1.661x | 10.91 | 0.989 | 10.860~15.568 |
| | Nematode J$_2$ | y = −1.637 + 1.726x | 12.25 | 0.997 | 7.699~13.190 |
| Compound 17 | Nematode eggs | y = −1.532 + 1.612x | 9.68 | 0.991 | 6.420~9.248 |
| | Nematode J$_2$ | y = −1.654 + 1.346x | 12.85 | 0.994 | 6.645~9.850 |
| Compound 18 | Nematode eggs | y = −1.513 + 1.121x | 10.23 | 0.984 | 6.812~9.514 |
| | Nematode J$_2$ | y = −1.437 + 1.456x | 12.47 | 0.992 | 6.628~9.191 |
| Compound 19 | Nematode eggs | y = −1.126 + 1.113x | 15.21 | 0.991 | 6.827~9.557 |
| | Nematode J$_2$ | y = −1.647 + 1.734x | 17.24 | 0.988 | 8.699~11.190 |
| Compound 20 | Nematode eggs | y = −1.568 + 1.558x | 10.143 | 0.982 | 8.490~12.133 |
| | Nematode J$_2$ | y = −1.736 + 1.581x | 12.532 | 0.998 | 10.533~15.084 |
| Compound 21 | Nematode eggs | y = −1.512 + 1.231x | 11.98 | 0.984 | 8.874~11.568 |
| | Nematode J$_2$ | y = −1.654 + 1.126x | 13.74 | 0.991 | 7.625~9.452 |
| Compound 22 | Nematode eggs | y = −1.126 + 1.131x | 9.57 | 0.984 | 12.860~15.560 |
| | Nematode J$_2$ | y = −1.237 + 1.146x | 10.85 | 0.994 | 6.614~9.187 |
| Compound 23 | Nematode eggs | y = −1.326 + 1.181x | 10.23 | 0.985 | 6.140~9.278 |
| | Nematode J$_2$ | y = −1.657 + 1.236x | 11.24 | 0.990 | 8.699~10.142 |
| Compound 24 | Nematode eggs | y = −1.236 + 1.211x | 10.91 | 0.995 | 7.807~9.128 |
| | Nematode J$_2$ | y = −1.147 + 1.516x | 12.24 | 0.989 | 8.614~10.124 |
| Compound 25 | Nematode eggs | y = −1.126 + 1.431x | 13.91 | 0.990 | 8.812~9.524 |
| | Nematode J$_2$ | y = −1.987 + 1.126x | 15.74 | 0.991 | 9.624~12.190 |
| Compound 26 | Nematode eggs | y = −1.136 + 1.461x | 14.91 | 0.997 | 7.256~10.147 |
| | Nematode J$_2$ | y = −1.693 + 1.136x | 15.23 | 0.988 | 8.612~10.194 |
| Compound 27 | Nematode eggs | y = −1.536 + 1.691x | 7.85 | 0.994 | 6.860~9.568 |
| | Nematode J$_2$ | y = −1.607 + 1.796x | 8.91 | 0.998 | 6.699~9.190 |
| Compound 28 | Nematode eggs | y = −1.131 + 1.223x | 13.23 | 0.990 | 12.142~17.124 |
| | Nematode J$_2$ | y = −1.432 + 1.137x | 15.07 | 0.975 | 11.524~22.747 |
| Compound 29 | Nematode eggs | y = −1.121 + 1.232x | 12.24 | 0.996 | 12.555~18.105 |
| | Nematode J$_2$ | y = −1.349 + 1.247x | 13.86 | 0.990 | 11.598~22.721 |
| Compound 30 | Nematode eggs | y = −1.321 + 1.860x | 9.73 | 0.989 | 13.145~20.189 |
| | Nematode J$_2$ | y = −1.964 + 1.547x | 10.96 | 0.984 | 15.524~22.721 |
| Compound 31 | Nematode eggs | y = −1.491 + 1.250x | 9.60 | 0.982 | 12.555~20.170 |
| | Nematode J$_2$ | y = −1.919 + 1.557x | 10.07 | 0.954 | 11.598~29.720 |
| Compound 32 | Nematode eggs | y = −1.212 + 1.112x | 12.14 | 0.983 | 11.170~15.643 |
| | Nematode J$_2$ | y = −1.136 + 1.224x | 13.23 | 0.986 | 13.047~18.306 |
| Compound 33 | Nematode eggs | y = −1.579 + 1.286x | 12.08 | 0.986 | 10.190~16.253 |
| | Nematode J$_2$ | y = −1.236 + 1.224x | 13.37 | 0.997 | 11.877~17.996 |
| Compound 34 | Nematode eggs | y = −1.257 + 1.132x | 12.42 | 0.990 | 10.157~16.243 |
| | Nematode J$_2$ | y = −1.414 + 1.356x | 13.10 | 0.994 | 11.381~17.246 |
| Compound 35 | Nematode eggs | y = −1.224 + 1.116x | 10.84 | 0.982 | 10.141~16.243 |
| | Nematode J$_2$ | y = −1.412 + 1.225x | 11.67 | 0.992 | 11.547~17.086 |
| Compound 36 | Nematode eggs | y = −1.123 + 1.134x | 11.24 | 0.990 | 10.160~17.643 |
| | Nematode J$_2$ | y = −1.026 + 1.254x | 12.64 | 0.987 | 11.027~17.306 |
| Compound 37 | Nematode eggs | y = −1.259 + 1.136x | 12.84 | 0.993 | 10.170~16.643 |
| | Nematode J$_2$ | y = −1.426 + 1.256x | 13.67 | 0.976 | 11.047~17.396 |
| Compound 38 | Nematode eggs | y = −1.131 + 1.652x | 12.14 | 0.989 | 10.224~14.431 |
| | Nematode J$_2$ | y = −1.140 + 1.709x | 13.40 | 0.990 | 8.756~12.252 |
| Compound 39 | Nematode eggs | y = −1.121 + 1.692x | 11.85 | 0.994 | 10.249~14.531 |
| | Nematode J$_2$ | y = −1.430 + 1.129x | 13.40 | 0.991 | 9.726~13.202 |
| Compound 40 | Nematode eggs | y = −1.141 + 1.542x | 10.04 | 0.984 | 11.245~14.724 |
| | Nematode J$_2$ | y = −1.836 + 1.721x | 13.40 | 0.991 | 8.726~12.214 |
| Compound 41 | Nematode eggs | y = −1.431 + 1.322x | 11.41 | 0.986 | 10.299~15.231 |
| | Nematode J$_2$ | y = −1.213 + 1.743x | 13.86 | 0.984 | 9.726~13.202 |
| Compound 42 | Nematode eggs | y = −1.751 + 1.602x | 12.39 | 0.996 | 10.299~14.731 |
| | Nematode J$_2$ | y = −1.830 + 1.799x | 10.40 | 0.989 | 8.726~12.202 |
| Compound 43 | Nematode eggs | y = −1.123 + 1.276x | 11.98 | 0.986 | 8.152~11.168 |
| | Nematode J$_2$ | y = −1.312 + 1.321x | 13.35 | 0.991 | 12.158~19.242 |
| Compound 44 | Nematode eggs | y = −1.123 + 1.212x | 10.23 | 0.989 | 8.152~11.112 |
| | Nematode J$_2$ | y = −1.387 + 1.124x | 13.12 | 0.985 | 11.124~19.206 |
| Compound 45 | Nematode eggs | y = −1.132 + 1.214x | 10.14 | 0.974 | 8.152~12.158 |
| | Nematode J$_2$ | y = −1.326 + 1.231x | 12.35 | 0.984 | 12.198~19.206 |
| Compound 46 | Nematode eggs | y = −1.134 + 1.289x | 9.98 | 0.995 | 7.152~11.158 |
| | Nematode J$_2$ | y = −1.343 + 1.177x | 11.24 | 0.983 | 13.157~20.146 |
| Compound 47 | Nematode eggs | y = −1.134 + 1.431x | 11.41 | 0.984 | 7.232~11.358 |
| | Nematode J$_2$ | y = −1.146 + 1.681x | 12.24 | 0.995 | 12.158~19.276 |
| Compound 48 | Nematode eggs | y = −1.355 + 1.753x | 12.25 | 0.971 | 7.152~12.147 |
| | Nematode J$_2$ | y = −1.323 + 1.321x | 13.27 | 0.976 | 12.428~19.242 |
| Compound 49 | Nematode eggs | y = −1.123 + 1.212x | 10.36 | 0.985 | 9.152~15.108 |
| | Nematode J$_2$ | y = −1.335 + 1.124x | 11.35 | 0.975 | 13.378~21.206 |

TABLE 2-continued

Plant pathogenic nematode inhibition test results of compounds of nematocide containing lactonic ring

| Reagent | Test Object | Regression Equation | $LC_{50}$ (μg/ml) | Correlation Coefficient ($R^2$) | 95% Confidence Interval |
|---|---|---|---|---|---|
| Compound 50 | Nematode eggs | y = −1.121 + 1.673x | 12.75 | 0.990 | 8.152~12.168 |
|  | Nematode $J_2$ | y = −1.336 + 1.891x | 13.72 | 0.993 | 13.158~19.216 |
| Compound 51 | Nematode eggs | y = −1.113 + 1.226x | 12.23 | 0.995 | 8.152~12.158 |
|  | Nematode $J_2$ | y = −1.335 + 1.325x | 14.12 | 0.989 | 12.458~20.206 |
| Compound 52 | Nematode eggs | y = −1.325 + 1.265x | 10.12 | 0.990 | 8.152~12.108 |
|  | Nematode $J_2$ | y = −1.312 + 1.142x | 13.28 | 0.994 | 13.248~19.276 |
| Compound 53 | Nematode eggs | y = −1.175 + 1.233x | 8.98 | 0.995 | 7.152~11.158 |
|  | Nematode $J_2$ | y = −1.366 + 1.151x | 12.35 | 0.995 | 12.158~20.276 |
| Compound 54 | Nematode eggs | y = −1.124 + 1.148x | 12.40 | 0.912 | 8.650~10.245 |
|  | Nematode $J_2$ | y = −1.532 + 1.513x | 14.16 | 0.945 | 9.406~13.046 |
| Compound 55 | Nematode eggs | y = −1.168 + 1.214x | 13.24 | 0.933 | 6.156~10.428 |
|  | Nematode $J_2$ | y = −1.532 + 1.513x | 15.36 | 0.947 | 8.966~12.856 |
| Compound 56 | Nematode eggs | y = −1.124 + 1.210x | 11.56 | 0.985 | 6.056~10.235 |
|  | Nematode $J_2$ | y = −1.524 + 1.255x | 13.47 | 0.979 | 10.406~14.046 |
| Compound 57 | Nematode eggs | y = −1.114 + 1.214x | 12.12 | 0.991 | 8.654~10.425 |
|  | Nematode $J_2$ | y = −1.565 + 1.735x | 14.23 | 0.994 | 8.656~12.476 |
| Compound 58 | Nematode eggs | y = −1.645 + 1.118x | 10.07 | 0.984 | 7.656~10.415 |
|  | Nematode $J_2$ | y = −1.239 + 1.165x | 12.18 | 0.975 | 7.406~11.044 |
| Compound 59 | Nematode eggs | y = −1.113 + 1.245x | 11.24 | 0.982 | 9.623~16.415 |
|  | Nematode $J_2$ | y = −1.523 + 1.135x | 13.24 | 0.993 | 9.426~14.023 |
| Compound 60 | Nematode eggs | y = −1.135 + 1.228x | 8.40 | 0.977 | 6.656~10.435 |
|  | Nematode $J_2$ | y = −1.549 + 1.545x | 10.06 | 0.988 | 8.406~12.046 |

According to the data in Table 1, the compounds of the nematocide containing lactonic ring in the present invention have good control effects on the second-stage juveniles and eggs of nematodes, and have higher inhibition ratio on the hatch of nematode eggs than on the second-stage juveniles.

Toxicity Test

According to the earthworm and edaphon toxicity test procedures as prescribed in the *Test Guidelines on Environmental Safety Assessment for Chemical Pesticides*, earthworm and edaphon toxicity tests are conducted on compounds 1 to 60 from Table 1. The simulative usual dose of pesticide in the edaphon test is 40 ppm. The results of the two tests are as follows:

TABLE 2

Toxicity test results of compounds of nematocide containing lactonic ring

|  | Earthworm Toxicity LC50 (14 d) (Unit: mg/L) | Edaphon Toxicity (15 d) (Inhibition ratio when added amount is 100 times of usual dose) |
|---|---|---|
| Compound 1 | >10, low toxicity | <50%, low toxicity |
| Compound 2 | >10, low toxicity | <50%, low toxicity |
| Compound 3 | >10, low toxicity | <50%, low toxicity |
| Compound 4 | >10, low toxicity | <50%, low toxicity |
| Compound 5 | >10, low toxicity | <50%, low toxicity |
| Compound 6 | >10, low toxicity | <50%, low toxicity |
| Compound 7 | >10, low toxicity | <50%, low toxicity |
| Compound 8 | >10, low toxicity | <50%, low toxicity |
| Compound 9 | >10, low toxicity | <50%, low toxicity |
| Compound 10 | >10, low toxicity | <50%, low toxicity |
| Compound 11 | >10, low toxicity | <50%, low toxicity |
| Compound 12 | >10, low toxicity | <50%, low toxicity |
| Compound 13 | >10, low toxicity | <50%, low toxicity |
| Compound 14 | >10, low toxicity | <50%, low toxicity |
| Compound 15 | >10, low toxicity | <50%, low toxicity |
| Compound 16 | >10, low toxicity | <50%, low toxicity |
| Compound 17 | >10, low toxicity | <50%, low toxicity |
| Compound 18 | >10, low toxicity | <50%, low toxicity |
| Compound 19 | >10, low toxicity | <50%, low toxicity |
| Compound 20 | >10, low toxicity | <50%, low toxicity |
| Compound 21 | >10, low toxicity | <50%, low toxicity |
| Compound 22 | >10, low toxicity | <50%, low toxicity |
| Compound 23 | >10, low toxicity | <50%, low toxicity |
| Compound 24 | >10, low toxicity | <50%, low toxicity |
| Compound 25 | >10, low toxicity | <50%, low toxicity |
| Compound 26 | >10, low toxicity | <50%, low toxicity |
| Compound 27 | >10, low toxicity | <50%, low toxicity |
| Compound 28 | >10, low toxicity | <50%, low toxicity |
| Compound 29 | >10, low toxicity | <50%, low toxicity |
| Compound 30 | >10, low toxicity | <50%, low toxicity |
| Compound 31 | >10, low toxicity | <50%, low toxicity |
| Compound 32 | >10, low toxicity | <50%, low toxicity |
| Compound 33 | >10, low toxicity | <50%, low toxicity |
| Compound 34 | >10, low toxicity | <50%, low toxicity |
| Compound 35 | >10, low toxicity | <50%, low toxicity |
| Compound 36 | >10, low toxicity | <50%, low toxicity |
| Compound 37 | >10, low toxicity | <50%, low toxicity |
| Compound 38 | >10, low toxicity | <50%, low toxicity |
| Compound 39 | >10, low toxicity | <50%, low toxicity |
| Compound 40 | >10, low toxicity | <50%, low toxicity |
| Compound 41 | >10, low toxicity | <50%, low toxicity |
| Compound 42 | >10, low toxicity | <50%, low toxicity |
| Compound 43 | >10, low toxicity | <50%, low toxicity |
| Compound 44 | >10, low toxicity | <50%, low toxicity |
| Compound 45 | >10, low toxicity | <50%, low toxicity |
| Compound 46 | >10, low toxicity | <50%, low toxicity |
| Compound 47 | >10, low toxicity | <50%, low toxicity |
| Compound 48 | >10, low toxicity | <50%, low toxicity |
| Compound 49 | >10, low toxicity | <50%, low toxicity |
| Compound 50 | >10, low toxicity | <50%, low toxicity |
| Compound 51 | >10, low toxicity | <50%, low toxicity |
| Compound 52 | >10, low toxicity | <50%, low toxicity |
| Compound 53 | >10, low toxicity | <50%, low toxicity |

TABLE 2-continued

Toxicity test results of compounds of nematocide containing lactonic ring

| | Earthworm Toxicity LC50 (14 d) (Unit: mg/L) | Edaphon Toxicity (15 d) (Inhibition ratio when added amount is 100 times of usual dose) |
|---|---|---|
| Compound 54 | >10, low toxicity | <50%, low toxicity |
| Compound 55 | >10, low toxicity | <50%, low toxicity |
| Compound 56 | >10, low toxicity | <50%, low toxicity |
| Compound 57 | >10, low toxicity | <50%, low toxicity |
| Compound 58 | >10, low toxicity | <50%, low toxicity |
| Compound 59 | >10, low toxicity | <50%, low toxicity |
| Compound 60 | >10, low toxicity | <50%, low toxicity |

According to the data in Table 2, the compounds of the nematocide containing lactonic ring in the present invention are environment-friendly compounds, with low biotoxicity to soil environment and application safety.

The invention claimed is:

1. A nematocide having the following formula I:

General structural formula I

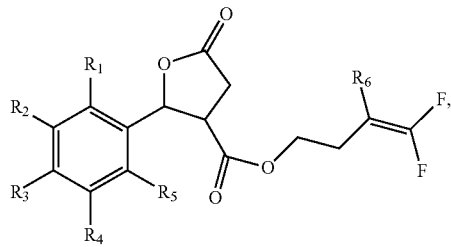

wherein $R_1$, $R_2$, $R_3$, $R_4$ and $R_5$ are selected from the group consisting of hydrogen, cyano, fluorine, chlorine, bromine, alkyl containing 1 to 4 carbon atoms, alkoxy containing 1 to 4 carbon atoms, alkoxyphenyl, alkoxy containing 1 to 4 carbon atoms and one or more chlorine atoms in place of hydrogen atoms on the carbon atoms, alkoxy containing 1 to 4 carbon atoms and one or more fluorine atoms in place of hydrogen atoms on the carbon atoms, nitryl, and amido; and $R_6$ is selected from the group the consisting of hydrogen, fluorine and chlorine.

2. The nematocide according to claim 1, wherein $R_6$ is fluorine atom.

3. The nematocide according to claim 2, wherein $R_1$=$CF_3$, and $R_2$=$R_3$=$R_4$=$R_5$=H.

4. The nematocide according to claim 2, wherein $R_1$=$OCF_3$, and $R_2$=$R_3$=$R_4$=$R_5$=H.

5. The nematocide according to claim 2, wherein $R_1$=$R_2$=$R_5$=H, $R_3$=F, and $R_4$=—O—$C_6H_5$.

6. The nematocide according to claim 2, wherein $R_2$=$R_4$=$CF_3$, and =$R_3$=$R_5$=H.

7. A method for preparing the nematocide according to claim 1, comprising the following steps of: adding

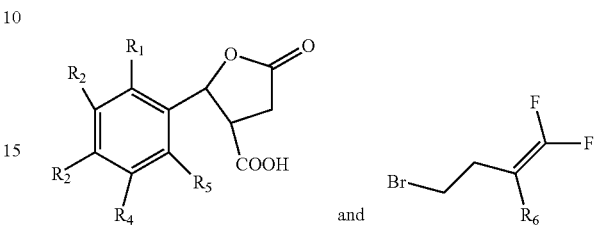

into a solvent, and adding an acid-binding agent; maintaining stirring for 22 to 26 hours at a temperature of 20 to 30° C.; distilling under vacuum at a pressure of 0.08 to 0.10 kPa to remove the solvent; adding methylene dichloride and water, and evenly stirring; carrying out static stratification to remove water; and distilling under vacuum at a pressure of 0.08 to 0.10 kPa to remove the methylene dichloride, thus obtaining the nematocide, as shown in formula I, wherein

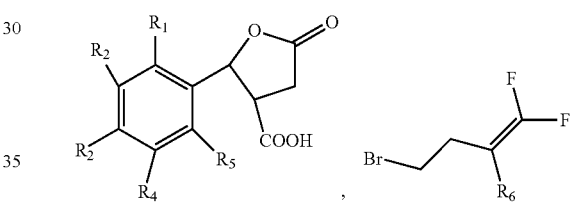

and the acid-binding agent have a molar ratio of 1:0.8 to 1.2:3 to 5;

$R_1$, $R_2$, $R_3$, $R_4$, $R_5$, and $R_6$ are the same as above;

the solvent is selected from the group consisting of methyl alcohol, ethyl alcohol, acetone, N, N-dimethylformamide and N, N-dimethylformamide; and the acid-binding agent is selected from the group consisting of potassium carbonate, sodium carbonate, pyridine and triethylamine.

8. A method of controlling a nematode disease in agriculture comprising applying the nematocide according to claim 1 to crops, plants, soil, nematodes, nematode eggs, or a combination thereof.

* * * * *